United States Patent [19]

Divjak

[11] Patent Number: 5,782,245
[45] Date of Patent: Jul. 21, 1998

[54] PROCEDURE OF ELABORATING ONE-PIECE CUSTOM POSTS ON NON-PARALLEL ROOTED TEETH

[75] Inventor: Milan Divjak, Celje, Slovenia

[73] Assignee: Chris Company, Inc., Ridgewood, N.J.

[21] Appl. No.: 759,261

[22] Filed: Dec. 2, 1996

[51] Int. Cl.⁶ .................................................. A61B 19/00
[52] U.S. Cl. ............................ 128/898; 433/219; 433/220
[58] Field of Search ................................ 128/898; 433/173, 433/219, 220, 221, 224, 225

[56] References Cited

U.S. PATENT DOCUMENTS

| 3,962,787 | 6/1976 | Corbett | 433/220 |
| 4,348,182 | 9/1982 | Shirota | 433/214 |
| 5,035,620 | 7/1991 | Roane | 433/221 |

FOREIGN PATENT DOCUMENTS

| 3037800 | 4/1981 | Germany | 433/224 |
| 0806021 | 2/1981 | U.S.S.R. | 433/221 |

Primary Examiner—Kimberly L. Asher
Assistant Examiner—Kelly O'Hara
Attorney, Agent, or Firm—Richard M. Goldberg

[57] ABSTRACT

A method of making a metal one-piece custom post member for non-parallel rooted teeth, including preparation of two root canals of the tooth by using a drill, making a funnel-shaped parallel fixing of entries in the root canals, inserting two posts made of burn-out plastic and sized to the root canals, into the canals, such that upper ends of the posts extend out therefrom, each plastic post having a body shaped as a partially flattened round stick, providing a flattened circle cross-section, one end thereof forming an enlarged cap shaped similarly to the body, treating upper ends of the posts that extend out of the canals with a self-curing resin to bind the posts together to form a plastic one-piece custom post member, removing the plastic one-piece custom post member from the tooth, casting a metal one-piece custom post member of the same size and dimensions from the plastic one-piece custom post member such that the metal one-piece custom post member has two metal posts extending therefrom, each being sufficiently thin so as to be flexible, and securing the cast metal one-piece custom post member in the tooth, with each metal post extending within one root canal, thereby dividing a required section of the tooth to attain a best possible tensile strength which is distributed over the two posts of the metal one-piece custom post.

2 Claims, 2 Drawing Sheets

PROCEDURE OF ELABORATING ONE-PIECE CUSTOM POSTS ON NON-PARALLEL ROOTED TEETH

BACKGROUND OF THE INVENTION

The subject of this patent is the procedure of elaborating one-piece custom posts on non-parallel rooted teeth, by using specially designed posts, made of burn-out plastic. The idea is to divided the required section so as to attain the appropriate tensile strength of the treatment over two posts, cast of soft plastic which allows impression and cementing treatment after casting of the one-piece custom post on non-parallel rooted teeth.

The technical problem which has successfully been solved by this procedure is to assure an efficient and well secured one-piece custom post that would exert a sufficiently great tensile strength on non-parallel rooted teeth.

Presently known solutions of this problem apply posts made of burn-out plastic, designed as stiff bodies that, after casting, can take over the function of chewing forces. In the case of a post with 0.9 mm diameter and 0.63 mm$^2$ section, and a casting, made out of standard dental alloy, with a tensile strength of 400N/mm$^2$, the withstanding resistance of the post, after cementing, equals 252N. Presently used posts, made of burn-out plastic, can also have greater diameters (0.9 to 1.8 mm), in order to adapt the post to a given breadth of the canals.

Considering the above stated facts, two procedures can be applied in order to solve the problem of casting a post, namely:

elaboration of a one-piece custom post, parallel fixed on two anchors, and elaboration of a two-piece custom post.

The disadvantage of the first procedure is the necessity to make a compromise on the account of dental tissue or the anchoring depth while the second solution gives the same quality as the procedure referred to in this patent application, but it requires a much more demanding technical realisation.

There is also a possibility of using ready-made posts, applying core materials, however, they do not belong to the category of custom posts.

SUMMARY OF THE INVENTION

The procedure referred to in this patent application enables the elaboration of a one-piece custom post on non-parallel rooted teeth, without making any compromise on the account of teeth tissue or anchoring depth.

The procedure of elaborating a one-piece custom post on non-parallel rooted teeth will be explained by giving an actual example of its realisation, illustrated in figures below.

DESCRIPTION OF THE PREFERRED EMBODIMENTS

In practice, the procedure of elaborating one-piece custom posts on non-parallel rooted teeth referred to in this patent application can be performed in four steps, illustrated in FIGS. 1a to 1d. The first step involves preparation of the root canals, using an adequate drill whereupon a funnel-shaped parallel fixing of entries into the canals is made. In the third step, the two post pieces, made of burn-out plastic, are inserted into the root canals, after being sized to the given length of each canal. Following the treatment of posts, self-curing resin is used so as to attain a one-piece custom post, shown in FIG. 1d. Owing to a special shape of the post bodies, seen in FIG. 2, they, upon cementing, allow deep penetration of the filling to the bottom of the canal, as well as elimination of surplus material, accumulated near the flat side of the post body.

Calculation of the tensile strength, described in the case of giving an example of the presently known technique of making a 0.9 mm diameter custom post, can be repeated also when using the procedure referred to in this patent application. In this case, it turns out that, upon cementing the posts, the obtained tensile strength, i.e. 256N is about the same, while the section of the two posts equals 0.64 mm$^2$.

Posts to be used by the procedure under this patent application, should be designed so that the body of the first post is oval, with parallel sides, onto which an asymmetrically shaped cap is added. The outstanding feature of such posts is that they are made of soft plastic which, upon casting (out of standard dental alloys) retain their flexibility. A post, tailored and shaped in this manner, practically always fits to a given situation in the first upper premolar.

As a rule, the depth preparation of the canals in the two roots is different, therefore, the posts should accordingly be cut to the appropriate size. In order to prevent mismatching of the posts while inserting them into the root canals, pairs of posts can be made in advance, fitted with a cap, marked or designed in a special way.

The posts to be elaborated under the procedure referred to in this patent application, can also have greater diameters but they are limited to a certain depth which still allows the required flexibility of the casting, made out of a specific alloy. When in a given situation, the diameter of the post prevents the application of this procedure, an endodontic treatment should be made around the plastic posts. Considering the fact that multiroot teeth usually have thin canals, a practical demand for this endodontic treatment is actually extremely rare.

Figure 1A:
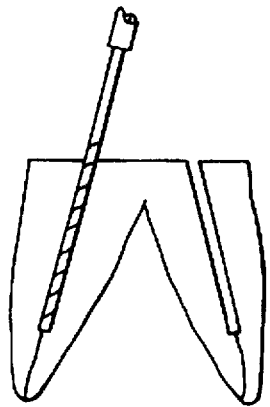
FIGS. 1a–1d illustrate the procedure of elaborating a post referred to in this patent application.
Figure 1B:
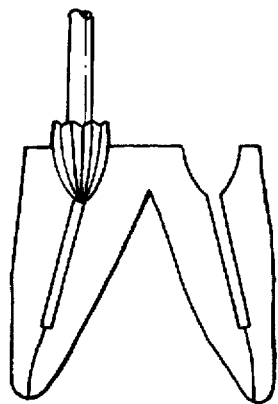
Figure 1C:
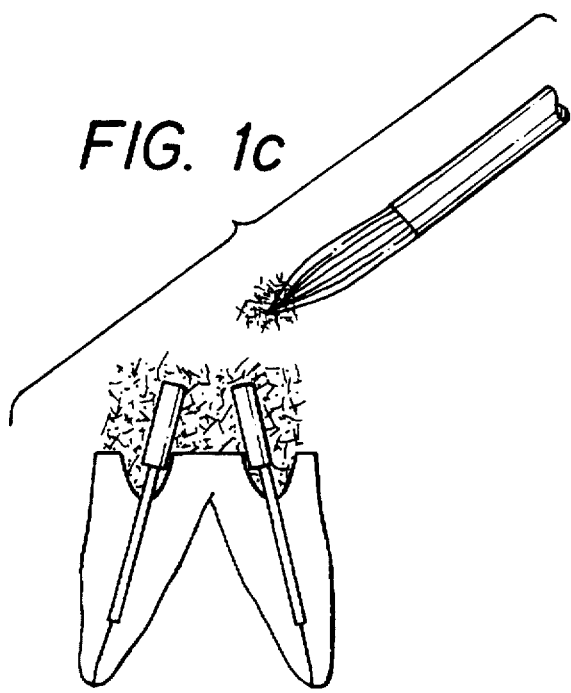
Figure 1D:
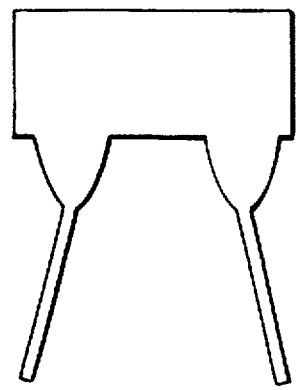
Figure 2A:
FIGS. 2a–2c are plastic burn-out posts with a cap, viewed from above, a side and below, respectively.
Figure 2B:
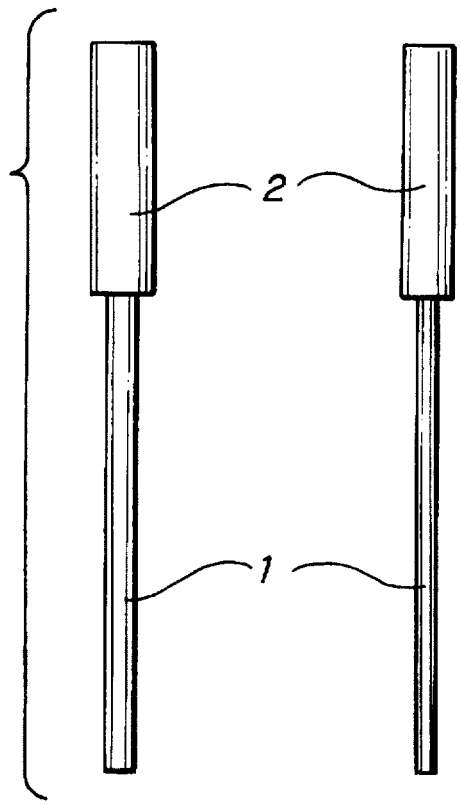
Figure 2C:

FIGS. 2a–2c show a post, seen from the two sides, above and below. It is made of burn-out plastic, and has a cap. It comprises a longish, thin, and round shaped body 1, and has two partially flattened facing sticks so that its section makes a flattened circle. One end of the body of post 1 is designed as a cap 2, and is shaped similarly as the body of post 1, but has greater dimensions. The flatness of the post can clearly be visible from the two pictures attached herewith.

This procedure of elaborating a one-piece custom post on non-parallel rooted teeth enables the realisation of posts, fixed on two anchors that are spaced apart, which results in more favorable chewing forces than applying a single anchor, with a section equal to two anchors spaced apart. In addition, it is possible to decrease the section of both anchors, though with very little practical significance.

What is claimed is:

1. A method of making a metal one-piece custom post member for non-parallel rooted teeth, comprising the steps of:

preparation of two root canals of the tooth by using a drill, making a funnel-shaped parallel fixing of entries in the root canals, inserting two posts made of burn-out plastic and sized respectively to the root canals, into the canals, such that upper ends of the posts extend out of the root canals, treating the upper ends of the posts that extend out of the root canals with a self-curing resin so as to bind the posts together to form a plastic one-piece custom post member, removing the plastic one-piece custom post member from the tooth, casting a metal one-piece custom post member from the plastic one-piece custom post member and of the same size and dimensions as the one-piece plastic post member such that said metal one-piece custom post member has two metal posts extending therefrom, each metal post being sufficiently thin so as to be flexible, and securing the cast metal one-piece custom post member in the tooth, with each metal post extending within one said root canal, thereby dividing a required section of the tooth to attain a best possible tensile strength which is distributed over the two posts of the metal one-piece custom post.

2. A method according to claim 1, wherein each burn-out plastic post has a body shaped as a partially flattened round stick, providing a cross-section of a flattened circle, and one end thereof forms a cap which is shaped similarly to the body of the post, but having a greater diameter than that of said body of said post.

* * * * *

UNITED STATES PATENT AND TRADEMARK OFFICE
CERTIFICATE OF CORRECTION

PATENT NO. : 5,782,245
DATED : July 21, 1998
INVENTOR(S) : Milan Divjak

It is certified that error appears in the above-indentified patent and that said Letters Patent is hereby corrected as shown below:

Title page, insert the priority data as follows:

-- Oct. 18, 1996 [SI] Slovenia  P-9600308 --.

Signed and Sealed this

Third Day of November, 1998

*Attest:*

BRUCE LEHMAN

*Attesting Officer*    *Commissioner of Patents and Trademarks*